United States Patent
Tanaka et al.

(10) Patent No.: US 9,228,181 B2
(45) Date of Patent: Jan. 5, 2016

(54) β-GLUCOSIDASE

(71) Applicant: HONDA MOTOR CO., LTD., Minato-Ku, Tokyo (JP)

(72) Inventors: Maiko Tanaka, Wako (JP); Shigenobu Mitsuzawa, Wako (JP); Satoru Shinkawa, Wako (JP); Daisuke Shibata, Kisarazu (JP); Takeshi Ara, Kisarazu (JP); Migiwa Takeda, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/323,893

(22) Filed: Jul. 3, 2014

(65) Prior Publication Data

US 2015/0017689 A1 Jan. 15, 2015

(30) Foreign Application Priority Data

Jul. 9, 2013 (JP) ................. 2013-143257

(51) Int. Cl.
*C12N 9/30* (2006.01)
*C12N 11/18* (2006.01)
*C12N 9/42* (2006.01)
*C12P 19/14* (2006.01)
*C12P 19/02* (2006.01)

(52) U.S. Cl.
CPC .............. *C12N 9/2445* (2013.01); *C12P 19/02* (2013.01); *C12P 19/14* (2013.01); *C12Y 302/01021* (2013.01)

(58) Field of Classification Search
None
See application file for complete search history.

(56) References Cited

U.S. PATENT DOCUMENTS

2004/0091469 A1    5/2004  Fukasawa et al.

FOREIGN PATENT DOCUMENTS

| EP | 2 468 859 A1 | 6/2012 |
| EP | 2 554 667 A1 | 2/2013 |
| JP | 2001-017180 A | 1/2001 |
| JP | 2010-148427 A | 7/2010 |
| WO | 2013/091544 A1 | 6/2013 |

OTHER PUBLICATIONS

Shiela E. Unkles et al., "The development of a homologous transformation system for Aspergillus oryzae based on the nitrate assimilation pathway: A convenient and general selection system for filamentous fungal transformation", Mol. Gen. Genet., vol. 218, pp. 99-104 (1989).

Extended EP Search Report with a mailing date of Nov. 7, 2014 in EP Patent Application 14175786.4.
Extended EP Search Report with a mailing date of Nov. 7, 2014 in EP Patent Application 14175789.8.
Prasetyo, Joni et al., "Response of Cellulase Activity in pH-controlled cultures of the filamentous fungus *Acremonium cellulolyticus*", Applied Biochemistry and Biotechnology, Humana Press, Inc. US, vol. 162, No. 1, Sep. 1, 2010, pp. 52-61.
Fuji, Tatsuya et al., "Enzymatic hydrolyzing performance of Acremonium cellulolyticus and Trichoderma reesei against three lignocellulosic materials", Biotechnology for Biofuels, Biomed Central Ltd, GB, vol. 2, No. 1, Oct. 1, 2009, p. 24.
Database UniProt [Online] Mar. 3, 2009, "SubName: Full=Beta-glucosidase {ECO: 0000313:EMBL:EED14314.1};".
Database UniProt [Online] Dec. 16, 2008, "SubName:Full=Beta-glucosidase {ECO: 0000313:EMBL:EEA19886.1};".
Database UniProt [Online} Mar. 3, 2009, "SubName: Full=Beta-glucosidase, putative {ECO:0000313:EMBL:EED21226.1} ; EC=3.2.1.21{ECO:0000313: EMBL:EED21226.1}; EC=3.2.1..21{ECO:0000313:EMBL:EED21226.1} ;".
Extended European search report, mailing date of Jan. 5, 2015, issued in EP Patent Application 14175790.6.
Extended European search report, mailing date of Jan. 5, 2015, issued in EP Patent Application 14175787.2.
Database UniProt [Online]Dec. 16, 2008 (Dec. 16, 2008), "SubName: Full=Beta-glucosidase 1, putatiive {ECO:00003131 EMBL:EEA28836.1 };", XP002733567, retrieved from EBI accession No. UNIPROT:B6Q884 Database accession No. B6Q884 *the whole document*.
Database EMBL [Online]Jan. 2, 2000 (Jan. 2, 2000), "Coccidioides immitis beta-glucosidase precursor (bgI2) gene, complete cds." XP002733568, retrieved from EBI accession No. EM STD: AF022893 Database accession No. AF022893 *the whole document*.
Database UniProt [Online]Dec. 16, 2008 (Dec. 16, 2008), "SubName: Full=Beta-glucosidase, putative {ECO:00003131 EMBL:EEA I9214.I};", XP002733544, retrieved from EBI accession No. UNIPROT:B6QW86 Database accession No. B6QW86 *the whole document*.

*Primary Examiner* — David J Steadman
(74) *Attorney, Agent, or Firm* — Carrier Blackman & Associates, P.C.; Joseph P. Carrier; Fulchand P. Shende

(57) ABSTRACT

The present invention relates to a polypeptide which has β-glucosidase activity, and which includes an amino acid sequence represented by SEQ ID NO: 1, a polypeptide including an amino acid sequence in which one or several amino acids are deleted, substituted, or added in the amino acid sequence represented by SEQ ID NO: 1, or a polypeptide including an amino acid sequence having 90% or greater sequence identity with the amino acid sequence represented by SEQ ID NO: 1. According to the present invention, a novel β-glucosidase enzyme derived from *Acremonium* cellulolyticus, a polynucleotide encoding the β-glucosidase, an expression vector for expressing the β-glucosidase, a transformant incorporated with that expression vector, and a method for producing a cellulose degradation product using the β-glucosidase can be provided.

4 Claims, 4 Drawing Sheets

US 9,228,181 B2

β-GLUCOSIDASE

TECHNICAL FIELD

The present invention relates to a β-glucosidase enzyme derived from *Acremonium* cellulolyticus. More particularly, the present invention relates to a novel β-glucosidase, a polynucleotide that encodes the β-glucosidase, an expression vector for expressing the β-glucosidase, a transformant incorporated with the expression vector, and a method for producing a cellulose degradation product using the β-glucosidase.

The present application claims priority on the basis of Japanese Patent Application No. 2013-143257, filed on Jul. 9, 2013, the contents of which are incorporated herein by reference.

BACKGROUND ART

Recently, the development of alternative energy to oil is a very important issue, because of the concern related to transportation energy supply, such as large increases in oil prices and the petroleum depletion prediction in the near future (peak oil), as well as environmental problems such as global warming and aerial pollution. Plant biomass, or lignocellulose, is the most plentiful renewable energy source on earth, which is expected to serve as an alternative source to oil. The main components in the dry weight of biomass are polysaccharides such as celluloses and hemicelluloses, and lignin. For example, polysaccharides are used as a biofuel or a raw material of chemical products, after being hydrolyzed into monosaccharides such as glucose or xylose by hydrolases which are collectively referred to as cellulase enzymes. Consequently, in the field of biorefining, it is important to develop a diverse range of highly active cellulase enzymes in order to efficiently carry out enzymatic hydrolysis treatment on cellulose-based biomass.

Lignocellulose is recalcitrant due to its highly complicated structures, and is hard to degrade with a single cellulolytic enzyme. Lignocellulose degradation to sugar requires at least three types of enzymes: endoglucanases (cellulase or endo-1,4-β-D-glucanase, EC 3.2.1.4) which randomly cut internal sites on cellulose chain, cellobiohydrolases (1,4-β-cellobiosidase or cellobiohydrolase, EC 3.2.1.91) which act as an exo-cellulase on the reducing or non-reducing ends of cellulose chain and release cellobiose as major products, and β-glucosidases (EC 3.2.1.21) which hydrolyze cellobiose to glucose. Besides, it is thought to be necessary to have an appropriate blending of a plurality of enzymes including xylanase (endo-1,4-β-xylanase, EC 3.2.1.8) which is a hemicellulase and other plant cell wall degrading enzymes.

On the other hand, *Acremonium* cellulolyticus is a filamentous fungus that produces a potent hydrolytic cellulase, and two types of cellobiohydrolase genes, 3 types of β-glucosidase genes and 7 types of endoglucanase genes have currently been isolated therefrom (see, for example, Patent Document 1). Endoglucanase is one of the glycoside hydrolases associated with the process of producing monosaccharides by randomly cleaving and degrading celluloses or lignocelluloses such as hemicellulose.

PRIOR ART DOCUMENTS

Patent Documents

[Patent Document 1] Japanese Unexamined Patent Application, First Publication No. 2010-148427

DISCLOSURE OF THE INVENTION

Problems to be Solved by the Invention

An object of the present invention is to provide a novel β-glucosidase derived from *Acremonium* cellulolyticus, a polynucleotide that encodes the β-glucosidase, an expression vector for expressing the β-glucosidase, a transformant incorporated with the expression vector, and a method for producing a cellulose degradation product using the β-glucosidase.

Means for Solving the Problems

As a result of conducting extensive studies to develop a novel cellulase enzyme having high activity, the inventors of the present invention isolated and identified a novel cellulase gene from *Acremonium* cellulolyticus, thereby leading to completion of the present invention.

[1] A first aspect of the present invention is:
a β-glucosidase having a β-glucosidase catalytic domain which includes: (A) a polypeptide including the amino acid sequence represented by SEQ ID NO. 1; (B) a polypeptide having β-glucosidase activity including an amino acid sequence obtained by deleting, substituting or adding one or a plurality of amino acids in the amino acid sequence represented by SEQ ID NO: 1; or (C) a polypeptide including an amino acid sequence having 90% or greater sequence identity with the amino acid sequence represented by SEQ ID NO: 1, and having β-glucosidase activity.

[2] The β-glucosidase of [1] above preferably has β-glucosidase activity at pH 3.0 to pH 5.5 and at a temperature of 30° C. to 45° C. that uses p-Nitrophenyl β-D-glucopyranoside as a substrate.

[3] A second aspect of the present invention is a polynucleotide including a region that encodes a β-glucosidase catalytic domain which includes: (a) a base sequence that encodes a polypeptide including the amino acid sequence represented by SEQ ID NO: 1; (b) a base sequence that encodes a polypeptide including an amino acid sequence in which one or several amino acids are deleted, substituted, or added in the amino acid sequence represented by SEQ ID NO: 1, and having β-glucosidase activity; (c) a base sequence that encodes a polypeptide including an amino acid sequence having 90% or greater sequence identity with the amino acid sequence represented by SEQ ID NO: 1, and having β-glucosidase activity; or (d) a base sequence of a polynucleotide which hybridizes with a polynucleotide comprising the base sequence represented by SEQ ID NO: 2 under a stringent condition, and being a base sequence that encodes a polypeptide having β-glucosidase activity.

[4] A third aspect of the present invention is an expression vector, which is incorporated with the polynucleotide described in [3] above, and which is able to express a polypeptide having β-glucosidase activity in a host cell.

[5] A fourth aspect of the present invention is a transformant, which is introduced with the expression vector described in [2] above.

[6] The transformant described in [5] above is preferably a eukaryotic microbe.

[7] The transformant described in [5] above is preferably a filamentous fungus.

[8] A fifth aspect of the present invention is a method for producing a β-glucosidase, including: generating a polypeptide having β-glucosidase activity in the transformant described in any one of [5] to [7] above.

[9] A sixth aspect of the present invention is a cellulase mixture, including: the β-glucosidase described in [1] or [2]

above or a β-glucosidase produced by the method for producing a β-glucosidase described in [8] above, and at least one type of other cellulases.

[10] A seventh aspect of the present invention is a method for producing a cellulose degradation product including generating a cellulose degradation product by contacting a cellulose-containing material with the β-glucosidase described in [1] or [2] above or a β-glucosidase produced by the method for producing a β-glucosidase described in [8] above.

[11] In the method for producing a cellulose degradation product described in [10] above, at least one type of other cellulases are preferably further contacted with the cellulose-containing material.

[12] In the method for producing a cellulose degradation product described in [10] above, a cellobiohydrolase including an amino acid sequence represented by SEQ ID NO: 12 and an endoglucanase including an amino acid sequence represented by SEQ ID NO: 13 are preferably further contacted with the cellulose-containing material.

[13] In the method for producing a cellulose degradation product described in [10] above, a cellobiohydrolase including an amino acid sequence represented by SEQ ID NO: 12, an endoglucanase comprising an amino acid sequence represented by SEQ ID NO: 13, and at least one type of hemicellulases are preferably further contacted with the cellulose-containing material.

Effects of the Invention

The β-glucosidase according to the present invention is a novel β-glucosidase enzyme derived from *Acremonium* cellulolyticus. Since this β-glucosidase has hydrolase activity on cellulose, it is particularly preferable for enzymatic hydrolysis treatment of cellulose-based biomass.

In addition, the polynucleotide, the expression vector incorporated with the polynucleotide, and the transformant introduced with the expression vector according to the present invention are preferably used in the production of the β-glucosidase according to the present invention.

BEST MODE FOR CARRYING OUT THE INVENTION

β-Glucosidase

Figure 1:
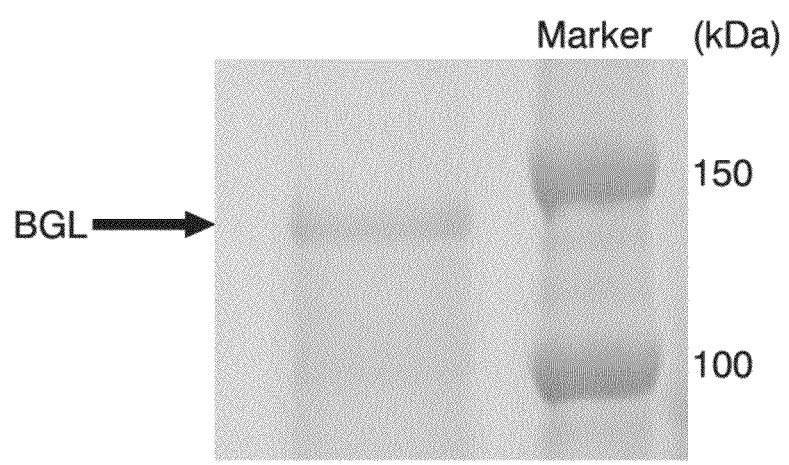
FIG. 1 shows the SDS-PAGE analysis result of the enzyme sample (BGL) in Example 1.

The inventors of the present invention isolated and identified a gene encoding a novel β-glucosidase from cDNA synthesized by a reverse transcription reaction using mRNA recovered from *Acremonium* cellulolyticus as template, designated that gene as BGL gene, and designated β-glucosidase encoded by that gene as BGL. The amino acid sequence of BGL is shown in SEQ ID NO: 1, and the base sequence encoding BGL (base sequence of the coding region of BGL gene) is shown in SEQ ID NO: 2.

In general, in a protein having some kind of bioactivity, one or 2 or more of amino acids can be deleted, substituted, or added without deteriorating the bioactivity. That is, in BGL, one or 2 or more of amino acids can also be deleted, substituted, or added without deteriorating the β-glucosidase activity.

That is, the β-glucosidase of a first aspect of the present invention is a β-glucosidase having a β-glucosidase catalytic domain which includes any one of (A) to (C) indicated below:

(A) a polypeptide including the amino acid sequence represented by SEQ ID NO. 1;

(B) a polypeptide including an amino acid sequence in which one or several amino acids are deleted, substituted, or added in the amino acid sequence represented by SEQ ID NO: 1, and having β-glucosidase activity; or (C) a polypeptide including an amino acid sequence having 90% or greater sequence identity with the amino acid sequence represented by SEQ ID NO: 1, and having β-glucosidase activity.

In the present invention and description of the present application, the deletion of an amino acid in a polypeptide refers to the deletion (or removal) of a portion of the amino acids that compose a polypeptide.

In the present invention and description of the present application, the substitution of an amino acid in a polypeptide refers to the substitution of an amino acid that composes a polypeptide with another amino acid.

In the present invention and description of the present application, the addition of an amino acid in a polypeptide refers to the insertion of a new amino acid in a polypeptide.

In the polypeptide of the aforementioned (B), the number of amino acids to be deleted, substituted, or added in the amino acid sequence represented by SEQ ID NO: 1 is preferably 1 to 20, more preferably 1 to 10 and even more preferably 1 to 5. The position(s) of the amino acid(s) to be deleted, substituted, or added in each amino acid sequence is (are) not specifically limited as long as the polypeptide including the amino acid sequence in which amino acids have been deleted, substituted, or added retains β-glucosidase activity.

In the polypeptide of the aforementioned (C), although there are no particular limitations on the sequence identity with the amino acid sequence represented by SEQ ID NO: 1 is not specifically limited as long as it is 901 or greater and less than 100%, although it is preferable to be 93% or greater and less than 100%, more preferably 95% or greater and less than 100%, and even more preferably 98% or greater and less than 100%.

Note that, the sequence identity (homology) between two amino acid sequences is obtained such that: the two amino acid sequences are juxtaposed while having gaps in some parts accounting for insertion and deletion so that the largest number of corresponding amino acids can be matched, and the sequence identity is deemed to be the proportion of the matched amino acids to the whole amino acid sequences excluding the gaps, in the resulting alignment. The sequence identity between amino acid sequences can be obtained by using a variety of homology search software commonly known in the art. The sequence identity value of amino acid sequences in the present invention is obtained by calculation on the basis of an alignment obtained from the maximum matching function of the publicly known homology search software, Genetyx Ver. 11.0.

The polypeptides of the aforementioned (B) and (C) may be artificially designed, or may also be homologues of BGL, or partial proteins thereof.

The polypeptides of the aforementioned (A) to (C) may be respectively synthesized in a chemical manner based on the amino acid sequence, or may also be produced by a protein expression system using the polynucleotide according to the second aspect of the present invention that will be described later. In addition, the polypeptides of the aforementioned (B) and (C) can also be respectively synthesized artificially based on a polypeptide including the amino acid sequence represented by SEQ ID NO: 1, by using a gene recombination technique to introduce amino acid mutation(s).

The β-glucosidase according to the present invention uses a glucan containing a β-glycoside bond as a substrate. Examples of substrates of the β-glucosidase according to the present invention include crystalline cellulose, carboxymethyl cellulose (CMC), glucans composed of β-1,4 bonds such as cellobiose, glucans composed of β-1,3 bonds and β-1,4 bonds, and glucans composed of β-1,6 bonds such as gentiobiose.

The β-glucosidase according to the present invention exhibits β-glucosidase activity within a temperature range of 30° C. to 45° C. The β-glucosidase according to the present invention exhibiting β-glucosidase activity within a temperature range of 25° C. to 55° C. is preferable, and within a temperature range of 20° C. to 60° C. is more preferable. Moreover, the β-glucosidase having an optimum temperature range of β-glucosidase activity according to the present invention within a temperature range of 25° C. to 55° C. is preferable, within a temperature range of 30° C. to 50° C. is more preferable, within a temperature range of 40° C. to 50° C. is ever more preferable.

The β-glucosidase activity according to the present invention refers to activity that uses a glucan containing a β-glycoside bond as a substrate and forms a monosaccharide by hydrolyzing the aforementioned substrate.

Although varying depending on the reaction temperature, the optimum pH of the β-glucosidase according to the present invention is within the range of pH 4.0 to pH 6.0, preferably within the range of pH 4.0 to pH 6.0, more preferably within the range of pH 4.5 to pH 6.0. The β-glucosidase according to the present invention preferably exhibits β-glucosidase activity at least within the range of pH 4.5 to pH 5.5, preferably within the range of pH 3.0 to pH 5.5, and more preferably within the range of pH 2.5 to pH 6.0.

The β-glucosidase according to the present invention may also have cellulose hydrolysis activity other than β-glucosidase activity. Examples of other cellulose hydrolysis activity include cellobiohydrolase activity, endoglucanase activity and xylanase activity.

The β-glucosidase according to the present invention may be an enzyme consisting only of a β-glucosidase catalytic domain which includes any one of the polypeptides of the aforementioned (A) to (C), or may also include other regions. Examples of other regions include regions other than a β-glucosidase catalytic domain of a known β-glucosidase. For example, the β-glucosidase according to the present invention also includes an enzyme obtained by substituting a β-glucosidase catalytic domain in a known β-glucosidase with a polypeptide of the aforementioned (A) to (C).

The β-glucosidase according to the present invention may also have a signal peptide able to transport it to a specific region to effect localization within a cell, or a signal peptide to effect extracellular secretion, for example, at the N-terminal or C-terminal thereof. Examples of such signal peptides include endoplasmic reticulum signal peptide, a nuclear transport signal peptide and a secretory signal peptide. The addition of a signal peptide to the N-terminal or C-terminal of the aforementioned β-glucosidase allows β-glucosidase expressed in a transformant to be secreted outside a cell or localized in the endoplasmic reticulum or other locations in a cell.

The endoplasmic reticulum retention signal peptide is not particularly limited, as long as it is a peptide enabling to retain the polypeptide within the endoplasmic reticulum, and a publicly known endoplasmic reticulum retention signal peptide can be appropriately used. The endoplasmic reticulum retention signal peptide can be exemplified by, for example, a signal peptide including a HDEL amino acid sequence, or the like.

In addition, various types of tags may be added to, for example, the N-terminal or C-terminal of the β-glucosidase according to the present invention, so as to enable easy and convenient purification in the case of having produced the aforementioned β-glucosidase using an expression system. Examples of tags used include those commonly used in the expression or purification of recombinant protein, such as a His tag, a HA (hemagglutinin) tag, a Myc tag or a Flag tag.

Moreover, the β-glucosidase according to the present invention may also have other functional domains provided β-glucosidase activity derived from the polypeptides of the aforementioned (A) to (C) is not impaired. Examples of other functional domains include cellulose binding modules. Examples of the cellulose binding modules include cellulose binding modules retained by a known protein or those that have undergone suitable modification.

In the case the β-glucosidase according to the present invention has a functional domain other than a β-glucosidase catalytic domain, the other functional domain may be located upstream (N-terminal side) or downstream (C-terminal side) from the β-glucosidase catalytic domain. In addition, the other functional domain and the β-glucosidase catalytic domain may be directly linked, or linked via a linker sequence of an appropriate length.

[Polynucleotide that Encodes β-Glucosidase]

The polynucleotide of a second aspect of the present invention encodes the β-glucosidase of the first aspect of the present invention. This β-glucosidase can be produced by using an expression system of a host by introducing an expression vector incorporated with the polynucleotide into the host.

More specifically, the polynucleotide of the second aspect of the present invention is a polynucleotide having a region that encodes a β-glucosidase catalytic domain which includes any one of the following base sequences (a) to (d):

(a) a base sequence that encodes a polypeptide including the amino acid sequence represented by SEQ ID NO: 1;

(b) a base sequence that encodes a polypeptide including an amino acid sequence in which one or several amino acids are deleted, substituted, or added in the amino acid sequence represented by SEQ ID NO: 1, as well as having β-glucosidase activity;

(c) a base sequence that encodes a polypeptide including an amino acid sequence having 90% or greater sequence identity with the amino acid sequence represented by SEQ ID NO: 1, as well as having β-glucosidase activity; or (d) a base sequence of a polynucleotide that hybridizes under stringent conditions with a polynucleotide including the base sequence represented by SEQ ID NO: 2, as well as being a base sequence that encodes a polypeptide having β-glucosidase activity.

Note that, the sequence identity (homology) between two base sequences is obtained such that: the two base sequences are juxtaposed while having gaps in some parts accounting for insertion and deletion so that the largest number of corresponding bases can be matched, and the sequence identity is deemed to be the proportion of the matched bases to the whole base sequences excluding the gaps, in the resulting alignment. The sequence identity between base sequences can be obtained by using a variety of homology search software commonly known in the art. The sequence identity value between base sequences in the present invention is obtained by calculation on the basis of an alignment obtained from the maximum matching function of the publicly known homology search software, Genetyx Ver. 11.0.

In addition, in the present invention and description of the present application, the term "stringent conditions" refers to, for example, the method described in NATURE PROTOCOL (VOL. 1, No, 2, p. 518 to 525) (Published online: 27 Jun. 2006, doi:10.1038/nprot.2006.73). An example thereof includes conditions under which hybridization is carried out by incubating for several hours to overnight at a temperature of 40° C. in a hybridization buffer composed of 6×SSC (composition of 20×SSC: 3M sodium chloride, 0.3 M citric acid solution), 5×Denhardt's solution (composition of 100×Denhardt's solution: 2% by mass bovine serum albumin, 2% by mass ficoll, 2% by mass polyvinylpyrrolidone), 0.5% by mass SDS, and 0.1mg/mL salmon sperm DNA.

Sequence identity of the base sequence of the aforementioned (d) with the base sequence represented by SEQ ID NO: 2 is, for example, 85% or greater and not greater than 100%, preferably 90% or greater and not greater than 100%, more preferably 93% or greater and not greater than 100%, and even more preferably 95% or greater and not greater than 100%.

In the base sequences of the aforementioned (a) to (d), a degenerate codon having a high frequency of usage in the host is preferably selected for the degenerate codon. For example, the base sequence of the aforementioned (a) may be a base sequence represented by SEQ ID NO: 2 or a base sequence that has been modified to a codon having a high frequency of usage in the host without altering the encoded amino acid sequence (SEQ ID NO: 1). Note that, these codons can be altered by a publicly known gene recombination technique.

The polynucleotide including the base sequence represented by SEQ ID NO: 2 may be chemically synthesized based on base sequence information, or may be obtained a region including a β-glucosidase catalytic domain in the BGL gene of *Acremonium* cellulolyticus from nature by using a gene recombination technique. The full length of the BGL gene or the partial region thereof can be obtained by, for example, collecting a sample containing *Acremonium* cellulolyticus from nature, using as template cDNA synthesized by a reverse transcription reaction by using mRNA recovered from the sample as a template, and carrying out PCR using a forward primer and reverse primer designed in accordance with ordinary methods based on the base sequence represented by SEQ ID NO: 2.

For example, the polynucleotides including the base sequence of the aforementioned (b), (c) or (d) can each be artificially synthesized by deleting, substituting or adding one or two or more of bases to a polynucleotide including the base sequence represented by SEQ ID NO: 2.

In the present invention and description of the present application, the deletion of a base in a polynucleotide refers to the deletion (or removal) of a portion of the nucleotides that compose a polypeptide.

In the present invention and description of the present application, the substitution of a base in a polynucleotide refers to the substitution of a base that composes a polynucleotide with another base.

In the present invention and description of the present application, the addition of a base in a polynucleotide refers to the insertion of a new base in a polynucleotide.

The polynucleotide of the second aspect of the present invention may only have a region that encodes a β-glucosidase catalytic domain, or may also have a region that encodes another functional domain such as a cellulose binding module, a linker sequence, various types of signal peptides, or various types of tags in addition to that region.

[Expression Vector]

The expression vector of the third aspect of the present invention is incorporated with the aforementioned polynucleotide of the second aspect of the present invention, and is capable of expressing a polypeptide having β-glucosidase activity in host cells. That is, the expression vector is an expression vector in which the aforementioned polynucleotide of the second aspect of the present invention is incorporated in a state that enables expression of the aforementioned β-glucosidase of the first aspect of the present invention.

In the present invention and description of the present application, an expression vector refers to a vector that contains DNA having a promoter sequence, DNA having a sequence for incorporating foreign DNA and DNA having a terminator sequence starting from the upstream side.

More specifically, an expression cassette including DNA having a promoter sequence, the aforementioned polynucleotide of the second aspect of the present invention, and DNA having a terminator sequence is required to be incorporated in the expression vector starting from the upstream side. Note that, the polynucleotide can be incorporated in the expression vector using well-known gene recombination technique. A commercially available expression vector preparation kit may also be used to incorporate the polynucleotide into the expression vector.

The expression vector may be that which is introduced into prokaryotic cells such as *Escherichia coli* or may be that which is introduced into eukaryotic cells such as yeast, filamentous fungi, cultured insect cells, cultured mammalian cells or plant cells. Arbitrary expression vectors normally used corresponding to each host can be used for these expression vectors.

An expression vector introduced into prokaryotic cells or an expression vector introduced into eukaryotic microbes such as yeast or filamentous fungi is preferable for the expression vector according to the present invention, an expression vector introduced into eukaryotic microbes is more preferable, an expression vector introduced into a filamentous fungus is even more preferable, and an expression vector introduced into *aspergillus* is even much more preferable. The use of an expression system in prokaryotic cells or eukaryotic microbes makes it possible to produce the β-glucosidase according to the present invention more easily and conveniently with high yield. In addition, since the β-glucosidase enzyme including the amino acid sequence represented by SEQ ID NO: 1 is an enzyme that is inherently possessed by the filamentous fungus *Acremonium* cellulolyticus, β-glucosidase can be synthesized that more closely approximates natural β-glucosidase by expressing the β-glucosidase using an expression system of a eukaryotic microbes such as filamentous fungus.

The expression vector according to the present invention is preferably an expression vector that is also incorporated with a drug resistance gene in addition to the aforementioned polynucleotide of the second aspect of the present invention. This is because it makes it easy to screen between host organisms that have been transformed by the expression vector and host organisms that have not been transformed. Examples of drug resistance genes include ampicillin resistance gene, kanamycin resistance gene, hygromycin resistance gene, or the like.

[Transformant]

The transformant of a fourth aspect of the present invention is introduced with the aforementioned expression vector of the third aspect of the present invention. The aforementioned β-glucosidase of the first aspect of the present invention can be expressed in this transformant. The β-glucosidase according to the present invention can be expressed in a wide range of expression hosts such as *Escherichia coli*, yeast, filamentous fungus or the chloroplasts of higher plants.

There are no particular limitations on the method used to prepare a transformant using an expression vector, and preparation can be carried out according to a method normally used in the case of preparing transformants. Examples of these methods include the PEG (polyethylene glycol)-calcium method, *Agrobacterium* method, particle gun method and electroporation, and the like. Among these, the PEG-calcium method or *Agrobacterium* method is preferable in the case the host is a filamentous fungus.

In the case of using prokaryotic cells, yeast, filamentous fungi, cultured insect cells or cultured mammalian cells and the like for the host, the resulting transformant can typically be cultured in accordance with ordinary methods in the same manner as the host prior to transformation.

Eukaryotic cells such as yeast, filamentous fungi, cultured insect cells or cultured mammalian cells and the like are preferable as hosts introduced with the expression vector. Since glycosylation modification is carried out on proteins in eukaryotic cells, the use of a transformant of eukaryotic cells enables the production of β-glucosidase having superior thermostable in comparison with the case of using a transformant of prokaryotic cells. In particular, in the case the transformant is a filamentous fungus such as an *aspergillus* and a eukaryotic microbe such as a filamentous fungus or yeast, β-glucosidase having superior thermostable can be produced comparatively easily and conveniently with high yield.

In the transformant according to the present invention, the expression cassette for expressing the β-glucosidase according to the present invention derived from the aforementioned expression vector of the third aspect of the present invention may be incorporated in a genome or may be present independently outside the genome.

[Method for Producing β-Glucosidase]

The method for producing β-glucosidase of a fifth aspect of the present invention is a method for producing β-glucosidase in the aforementioned transformant of the fourth aspect of the present invention. The β-glucosidase according to the present invention is constantly expressed in a transformant produced using an expression vector in which the aforementioned polynucleotide of the second aspect of the present invention is incorporated downstream from a promoter not having the ability to control the timing of expression and the like. On the other hand, by carrying out suitable induction treatment on a transformant producing a so-called expression inducible promoter, which induces expression according to a specific compound or temperature conditions and the like, under those respective conditions for inducing expression, β-glucosidase can be expressed in the concerned transformant.

There are no particular limitations on the method used to extract or purify β-glucosidase from the transformant provided it is a method that does not impair the activity of the β-glucosidase, and extraction can be carried out by a method normally used in the case of extracting polypeptides from cells or biological tissue. An example of such a method includes consists of immersing the transformant in a suitable extraction buffer to extract β-glucosidase followed by separating the extract and the solid residue. The extraction buffer preferably contains a solubilizing agent such as a surfactant. In the case the transformant is a plant, the transformant may be preliminarily shredded or crushed prior to immersing in extraction buffer. In addition, a known solid-liquid separation treatment can be used to separate the extract and solid residue, such as filtration, compression filtration or centrifugal separation, and the transformant may be pressed while still immersed in the extraction buffer. The β-glucosidase in the extract can be purified using a commonly known purification method such as salting-out, ultrafiltration or chromatography.

In the case the β-glucosidase according to the present invention has been expressed in a state of having a secretory signal peptide in the transformant, after having cultured the transformant, a solution can be easily and conveniently obtained that contains β-glucosidase by recovering culture supernatant from the resulting culture while excluding the transformant. In addition, in the case the β-glucosidase according to the present invention has a tag such as a His tag, β-glucosidase present in an extract or culture supernatant can be easily and conveniently purified by affinity chromatography utilizing that tag.

Namely, the method for producing β-glucosidase of the present invention includes the production of β-glucosidase in a transformant of the aforementioned fourth aspect of the present invention, and extraction and purification of the aforementioned β-glucosidase from the aforementioned transformant as desired.

[Cellulase Mixture]

The cellulase mixture of the sixth aspect of the present invention includes the aforementioned β-glucosidase of the first aspect of the present invention or β-glucosidase produced according to the aforementioned method for producing β-glucosidase of the fifth aspect of the present invention, and at least one type of other cellulases. The β-glucosidase produced according to the aforementioned method for producing β-glucosidase of the fifth aspect of the present invention may be in a state of being included in a transformant or may have been extracted or purified from a transformant. Glucans containing β-1,4 bonds such as cellulose can be degraded more efficiently by using the β-glucosidase according to the present invention in a cellulose degradation reaction in the form of a mixture with other cellulase.

There are no particular limitations on the cellulase other than the aforementioned β-glucosidase contained in the cellulase mixture provided it has cellulose hydrolysis activity.

Examples of cellulases other than the aforementioned β-glucosidase contained in the cellulase mixture include hemicellulases such as xylanase or β-xylosidase, endoglucanases, cellobiohydrolases, or the like. The cellulase mixture according to the present invention preferably contains at least one of hemicellulase and cellobiohydrolase, and more preferably contains both hemicellulase and cellobiohydrolase. In particular, the cellulase mixture preferably contains at least one or more types of cellulases selected from the group consisting of xylanase, β-xylosidase, endoglucanase and cellobiohydrolase, and more preferably contains all of xylanase, β-xylosidase, endoglucanase and cellobiohydrolase collectively.

[Method for Producing Cellulose Degradation Product]

The method for producing a cellulose degradation product of a seventh aspect of the present invention is a method for obtaining a degradation product by degrading cellulose with the β-glucosidase according to the present invention. More specifically, a cellulose degradation product is produced by contacting a material containing cellulose with the aforementioned β-glucosidase of the first aspect of the present invention, the aforementioned transformant of the fourth aspect of the present invention or β-glucosidase produced according to the aforementioned method for producing β-glucosidase of the fifth embodiment of the present invention.

There are no particular limitations on the material containing cellulose provided it contains cellulose. Examples of this material include cellulose biomass such as weeds or agricultural waste and used paper. The material containing cellulose is preferably subjected to physical treatment such as crushing or shredding, chemical treatment such as treatment with acid or alkali, or treatment by immersing or dissolving in a suitable buffer prior to contacting with the β-glucosidase according to the present invention.

The reaction conditions of the cellulose hydrolysis reaction carried out by the β-glucosidase according to the present invention are conditions that allow the β-glucosidase to exhibit β-glucosidase activity. For example, the reaction is preferably carried out at a temperature of 20° C. to 60° C. and a pH of 4 to 6 and more preferably carried out at a temperature of 25° C. to 55° C. at a pH of 4 to 6. The reaction time of the aforementioned hydrolysis reaction is suitably adjusted in consideration of such factors as the type of cellulose-containing material subjected to hydrolysis, the pretreatment method or the amount used. For example, the aforementioned hydrolysis reaction can be carried out over a reaction time of 10 minutes to 12 hours.

In addition to the β-glucosidase according to the present invention, at least one type of other cellulases are preferably used in the cellulose hydrolysis reaction. The same cellulases as those contained in the aforementioned cellulase mixture can be used for the other cellulases, and thermostable cellulase having cellulase activity at a temperature of 20° C. to 60° C. and a pH of 4 to 6 is preferable. In addition, the aforementioned cellulase mixture of the sixth aspect of the present invention may be used in the method for producing a cellulose degradation product instead of the aforementioned β-glucosidase of the first aspect of the present invention, the aforementioned transformant of the fourth aspect of the present invention, or β-glucosidase produced according to the aforementioned method for producing β-glucosidase of the fifth aspect of the present invention.

EXAMPLES

Although the following provides a more detailed explanation of the present invention by indicating examples thereof, the present invention is not limited to the following examples.

Example 1

(1) Construction of BGL *Aspergillus* Expression Vector
<Extraction of Genomic DNA of *Acremonium* Cellulolyticus>
*Acremonium* cellulolyticus strain H1 (acquired from the International Patent Organism Depository of the National Institute of Technology and Evaluation, accession number: FERM BP-11508, to be referred to as "strain H1") was inoculated onto PDB agar medium (plate medium obtained by adding 1.5% (w/v) of agarose to PDA medium (using Difco PDA broth)) followed by culturing for 1 week at a temperature of 30° C. The resulting bacterial cells were inoculated into PDA medium after cutting out the agar on which the cells were present to a diameter of 5 mm followed by shake-culturing at a temperature of 30° C. and 130 rpm. Bacterial cells recovered by centrifuging the culture for 10 minutes at 15000 rpm were washed twice with PDA medium to acquire a bacterial cell sample.

Beads were placed in a 2 mL volume plastic tube containing the bacterial cell sample, and crushing treatment for 90 seconds was repeated three times using a desktop bead-type crushing device (device name: Shake Master, Bio-Medical Science Co., Ltd.) to crush the bacterial cell sample followed by extracting DNA using Nucleon (Amersham Corp.).

<Genomic DNA of *Acremonium* Cellulolyticus BGL>
A sequence encoding BGL (SEQ ID NO: 3) was amplified by PCR using the resulting genomic DNA as template and using a primer including the base sequence represented by SEQ ID NO: 4 shown in Table 1, a primer including the base sequence represented by SEQ ID NO: 5, and DNA polymerase (trade name: KOD-Plus, Toyobo Co., Ltd.). PCR consisted of carrying out one cycle consisting of 2 minutes at a temperature of 94° C. followed by carrying out 30 cycles consisting of 20 seconds at a temperature of 96° C., 30 seconds at a temperature of 60° C. and 5 minutes at a temperature of 72° C. The resulting PCR product was purified using the QIAquick PXR Purification Kit (Qiagen Inc.).

<Determination of cDNA Sequence of *Acremonium* Cellulolyticus BGL>
Bacterial cells were prepared using the method described in the previously described section on <Extraction of Genomic DNA of *Acremonium* Cellulolyticus>. Next, beads were placed in a 2 mL volume plastic tube containing the bacterial cell sample, and crushing treatment for 90 seconds was repeated three times using a desktop bead-type crushing device (device name: Shake Master, Bio-Medical Science Co., Ltd.) to crush the bacterial cell sample followed by extracting RNA using Isogen II (Nippon Gene Co., Ltd.). cDNA was synthesized from the extracted RNA using a cDNA synthesis kit (trade name: SMARTer™ RACE cDNA Amplification Kit, Clontech Laboratories, Inc.). The resulting cDNA was subjected to sequence analysis and the resulting sequence (SEQ ID NO: 2) was compared with the genomic DNA sequence (SEQ ID NO: 3) to determine introns.

<Preparation of *E. Coli* Vector pBR-niaD Containing niaD Gene>
PCR was carried out in the same manner as amplification of BGL cDNA with the exception of using genomic cDNA of *Aspergillus oryzae* strain RIB40 (acquired from the National Institute of Technology and Evaluation, NBRC number: 100959, to be referred to as "strain RIB40") as template, and using a primer including the base sequence represented by SEQ ID NO: 6 shown in Table 1 and a primer including the base sequence represented by SEQ ID NO: 7 to amplify cDNA of nitrate reductase gene niaD derived from *Aspergillus oryzae*.

After digesting the resulting PCR amplification product and *E. coli* plasmid pBR322 (Takara Bio Inc.) using restriction enzymes AvaI and NdeI at a temperature of 37° C., the digestion products were separated by agarose gel electrophoresis, and the target band was cut out followed by extracting and purifying from that piece of gel using the QTAquick Gel Extraction Kit (Qiagen Inc.) to obtain cDNA restriction enzyme-treated fragments of pBR322 and niaD. These DNA fragments were then linked using a DNA Ligation Kit (Takara Bio Inc.) and an *E. coli* strain JM109 (to be referred to as "strain JM109") was transformed by these DNA fragments. As a result, a transformant was obtained that was introduced with plasmid pBR-niaD (plasmid having the cDNA fragment of niaD inserted between restriction enzymes AvaI and NdeI of pBR322).

<Incorporation of agdA Terminator in pBR-niaD>

PCR was carried out in the same manner as amplification of BGL cDNA with the exception of using genomic DNA of RIB40 as template, and using a primer including the base sequence represented by SEQ ID NO: 8 shown in Table 1 and a primer including the base sequence represented by SEQ ID NO: 9 to amplify cDNA of the terminator region of agdA gene derived from an *aspergillus* (to also be referred to as "agdA terminator").

After digesting the resulting PCR amplification product and pBR-niaD using restriction enzymes SalI and AvaI at a temperature of 37° C., cDNA restriction enzyme-treated fragments of pBR-niaD and agdA terminator were obtained from the resulting digestion product in the same manner as the aforementioned preparation of pBR-niaD, and these DNA fragments were linked and a strain JM109 was transformed by these DNA fragments. As a result, a transformant was obtained that was introduced with plasmid pBR-agdAT-niaD (plasmid having the cDNA fragment of the agdA terminator inserted between restriction enzyme SalI and AvaI of pBR322-niaD).

<Incorporation of enoA Promoter in pBR-agdAT-niaD>

PCR was carried out in the same manner as amplification of BGL cDNA with the exception of using genomic DNA of RIB40 as template, and using a primer including the base sequence represented by SEQ ID NO: 10 shown in Table 1 and a primer including the base sequence represented by SEQ ID NO: 11 to amplify cDNA of the promoter region of enoA gene derived from an *aspergillus* (to also be referred to as "enoA promoter").

After digesting the resulting PCR amplification product and pBR-agdAT-niaD using restriction enzymes NheI and SalI at a temperature of 37° C., cDNA restriction enzyme-treated fragments of pBR-agdAT-niaD and enoA promoter were obtained from the resulting digestion product in the same manner as the aforementioned preparation of pBR-niaD, and these DNA fragments were linked and a strain JM109 was transformed by these DNA fragments. As a result, a transformant was obtained that was introduced with plasmid pBR-enoAP-agdAT-niaD (plasmid having the cDNA fragment of the enoA promoter inserted between restriction enzymes NheI and SalI of pBR322-agdAT-niaD).

TABLE 1

| SEQ ID No. | Base Sequence |
|---|---|
| 4 | TCCTCCAAGTTACCCATGCGTGCATTCTGG |
| 5 | CGCTTCGTCGACCCCTTAAGATAAATCAGG |
| 6 | ATGCTCGGGAGCTTTGGATTTCCTACGTCTTC |
| 7 | ATGCATATGTCGAGAGTGTTGTGTGGGTCAACG |
| 8 | ATGGTCGACGAAGCGTAACAGGATAGCCTAGAC |
| 9 | ATGCCCGAGAGTAACCCATTCCCGGTTCTCTAG |
| 10 | ATGGCTAGCAGATCTCGCGGCAGGGTTGAC |
| 11 | ATGGTCGACCCCGGGTAACTTGGAGGACGGAAGAAAAGAG |

<Incorporation of BGL Genomic DNA in pBR-enoAP-agdAT-niaD>

First, after digesting pBR-enoAP-agdAT-niaD using restriction enzyme SalI at a temperature of 30° C., an SmaI-treated fragment of pBR-enoAP-agdAT-niaD was obtained from the resulting digestion product in the same manner as the aforementioned preparation of pBR-niaD.

The SmaI-treated fragment and a sequence encoding BGL purified in the manner previously described were linked using the In-Fusion™ HD Cloning Kit (Clontech Laboratories, Inc.) to obtain plasmid pBR-enoAP-BGL-adgAT-niaD (BGL *Aspergillus oryzae* expression vector), and Stellar Competent Cells (Clontech Laboratories, Inc.) were transformed by this plasmid and a BGL *E. coli* transformant was obtained. The resulting transformant was cultured overnight at a temperature of 37° C. and 180 rpm in LB medium containing 100 µg/mL, of ampicillin, and a large amount of pBR-enoAP-BGL-agdAT-niaD was prepared from the culture using the QIAquick Miniprep Kit (Qiagen Inc.).

(2) Production of *Aspergillus* Transformant Introduced with BGL *Aspergillus* Expression Vector

*Aspergillus oryzae* strain D300 (acquired from the National Institute of Technology and Evaluation) was transformed using the aforementioned plasmid pBR-enoAP-BGL-agdAT-niaD in accordance with the established PEG-calcium method (Mol. Gen. Genet., Vol. 218, pp. 99-104 (1989)). A transformant (BGL *aspergillus* transformed strain) was obtained by selecting the strain that was able to grow in Czapek-Dox medium (3% (w/v) dextrin, 0.1% (w/v) potassium dihydrogen phosphate, 0.2% (w/v) potassium chloride, 0.05% (w/v) magnesium sulfate, 0.001% (w/v) iron sulfate and 0.3% (w/v) sodium nitrate).

(3) Preparation of BGL from BGL *Aspergillus* Transformed Strain

The resulting BGL *aspergillus* transformed strain was allowed to form spores in Czapek-Dox medium followed by recovery of the spores in sterile water. The spores were inoculated into 100 mL of PD liquid medium contained in a 500 mL volume Erlenmeyer flask (2% (w/v) dextrin, 1% (w/v) polypeptone, 0.1% (w/v) casamino acids, 0.5% (w/v) potassium dihydrogen phosphate, 0.05% (w/v) magnesium sulfate and 0.1% (w/v) sodium nitrate) to a final spore concentration of $1 \times 10^4$/mL. After culturing the liquid for 3 days at a temperature of 30° C., the target gene product (BGL) was secreted and expressed in the medium. The culture liquid obtained after culturing was used as an enzyme sample.

BGL in the enzyme sample was confirmed by analysis by SDS-PAGE. SDS electrophoresis of the enzyme sample was carried out using 10% to 20% of Mini-Gradient gel (Atto Corp.). The enzyme sample and Tris-SDS β-ME sample treatment liquid (Atto Corp.) were mixed at a 1:1 ratio followed by treating for 5 minutes at a temperature of 100° C. and electrophoresing 20 µL of the mixture. Following completion of electrophoresis, the immobilized gel was stained with EzStain Aqua (Atto Corp.) to visualize the protein bands. Subsequently, an image of the gel was acquired using the ChemiDoc XRS Plus System (Bio-Rad Inc.). The acquired image was analyzed with Image Lab 2.0 software followed by quantification of the protein.

FIG. 1 shows the results of analyzing the enzyme sample (BGL) by SDS-PAGE. The right lane is the protein molecular weight marker, while the left lane is the enzyme sample. As a result, the enzyme sample was able to be confirmed to contain BGL having a molecular weight of approximately 130 kDa.

(4) Measurement of Enzyme Activity

Enzyme activity is indicated in units (U). 1 U is defined using the equation below as the amount of enzyme that produces 1 μmol of product from the substrate in 1 minute.

$$1\ U\ (\mu mol/min) = [\text{sugar formed }(\mu mol/L)] \times [\text{reaction liquid volume (L)}]/[\text{reaction time (min)}]$$

In addition, specific activity per 1 mg of protein is calculated using the following equation.

$$\text{Specific activity (U/mg)} = [\text{Units (U)}]/[\text{amount of protein (mg)}]$$

<Measurement of PNPG Degradation Activity>

PNPG (p-Nitrophenyl β-D-glucopyranoside) (Sigma-Aldrich Corp.) was used for the standard substrate. PNPG degradation activity is mainly used as an indicator β-glucosidase activity. In addition, a calibration curve was prepared from measured values of five dilution series (0 μM to 200 μM) prepared by suitably diluting a 1000 μmol/L PNP (p-nitrophenol) solution with 200 mM acetic acid buffer (pH 5.5).

More specifically, a number of 1.5 mL volume plastic tubes were first prepared equal to the number of samples measured, and liquids obtained by adding 615 μL of 200 mM acetic acid buffer (pH 5.5) and 50 μL of PNPG solution (3.4 mM, solvent: ultrapure water) to each tube followed by mixing well were adjusted to a temperature of 30° C. Next, 10 μL of enzyme sample were added to each tube to initiate the enzyme reaction, and after 15 minutes had elapsed since the start of the reaction, 625 μL of 0.2 M aqueous sodium carbonate solution were added and mixed to stop the reaction. Subsequently, 200 μl aliquots of the reaction solution were sampled from each tube followed by measuring the absorbance at 420 nm (A420). A sample treated in the same manner with the exception of adding 20 mM acetic acid buffer (pH 5.5) instead of enzyme sample was used as a blank during measurement of absorbance. PNP concentration was calculated from the A420 measured values and calibration curve, and specific activity was determined according to the equation below.

$$\text{Specific activity (U/mg)} = ([\text{PNP concentration }(\mu mol/L)] \times 0.001 \times 0.675/0.01)/(15 \times [\text{amount of protein (mg)}])$$

In addition, PNPG degradation activity was also measured in the same manner using BGL purified from a commercially available *Acremonium* species-derived hydrolysis enzyme mixture (trade name: Acremonium Cellulase, Meiji Seika Pharma Co., Ltd.) as a comparative example (to be referred to as "commercially available BGL").

As a result, in contrast to PNPG degradation activity (specific activity) being 20.3 U/mg in the case of the commercially available BGL used as a comparative example, the value was 32.1 U/mg in the case of BGL produced in the BGL *aspergillus* transformed strain. That is, the PNPG degradation activity of BGL produced in the BGL *aspergillus* transformed strain was more than 1.5 times higher than that of the commercially available BGL, and was confirmed to have superior β-glucosidase activity.

(5) Measurement of Hydrolysis Activity

The enzyme preparation used for measurement was prepared by containing the enzyme sample (BGL) prepared in the aforementioned section (3), cellobiohydrolase including the amino acid sequence represented by SEQ ID NO: 12, endoglucanase including the amino acid sequence represented by SEQ ID NO: 13, xylanase (*Thermoascus aurantiacus*-derived endo-1,4-beta-xylanase A, GenBank accession number: AAF24127) and β-xylosidase (*Thermotoga maritima*-derived β-xylosidase, Thermostable Enzyme Laboratory Co., Ltd.).

First, 25% (w/v) aqueous ammonia was mixed with finely crushed lignocellulose-based biomass in the form of corn stover to a weight ratio of 1:2.5 to obtain a substrate mixture containing corn stover and aqueous ammonia. Next, the aforementioned substrate mixture was held for 8 hours at a temperature of 80° C. to carry out hydrolysis pretreatment followed by separating the ammonia and adjusting to a pH of 4.5. Next, the corn stover content was adjusted to 20% by volume to obtain a hydrolysis pretreatment product used in the present example. The enzyme preparation containing BGL was added to this hydrolysis pretreatment product so that the final enzyme concentration per g of corn stover was 4.5 mg/g (corn stover) and allowed to react for 3 days at a temperature of 50° C. During the reaction, the reaction mixture was agitated by shaking at 160 rpm. In addition, a commercially available *Acremonium* species-derived hydrolysis enzyme mixture (trade name: Acremonium Cellulase, Meiji Seika Pharma Co., Ltd.) was used as a comparative control and allowed to react in the same manner.

Following completion of the reaction, the resulting hydrolysate was dispensed into a sampling tube and subjected to centrifugation treatment for 10 minutes at a temperature of 4° C. and 15,760×g. The resulting supernatant was transferred to a fresh 1.5 mL volume plastic tube, and after heat-treating for 5 minutes at a temperature of 95° C., was subjected to centrifugation treatment for 5 minutes at a temperature of 4° C. and 15,760×g. After again transferring the resulting supernatant to a fresh 1.5 mL volume plastic tube, the supernatant was filtered with a 0.2 μm (13 mm disk) filter. 0.2 mL of the filtrate were transferred to a vial, and sugar was detected by carrying out HPLC measurement under the conditions indicated below followed by evaluating sugar concentration. Glucose and xylose (Wako Pure Chemical Industries, Ltd., respectively) were used as sugar standards for HPLC.

Sugar concentration measurement device; Separator: Waters 2695 (Waters Corp.)

RI detector: Waters 2414 (Waters Corp.)

Column: Bio-Rad HPX-87P (Bio-Rad Inc.)

Sugar concentration measurement conditions:

Eluent: Ultrapure water

Flow rate: 0.6 mL/min

Column temperature: 85° C.

Detector temperature: 40° C.

Figure 2:
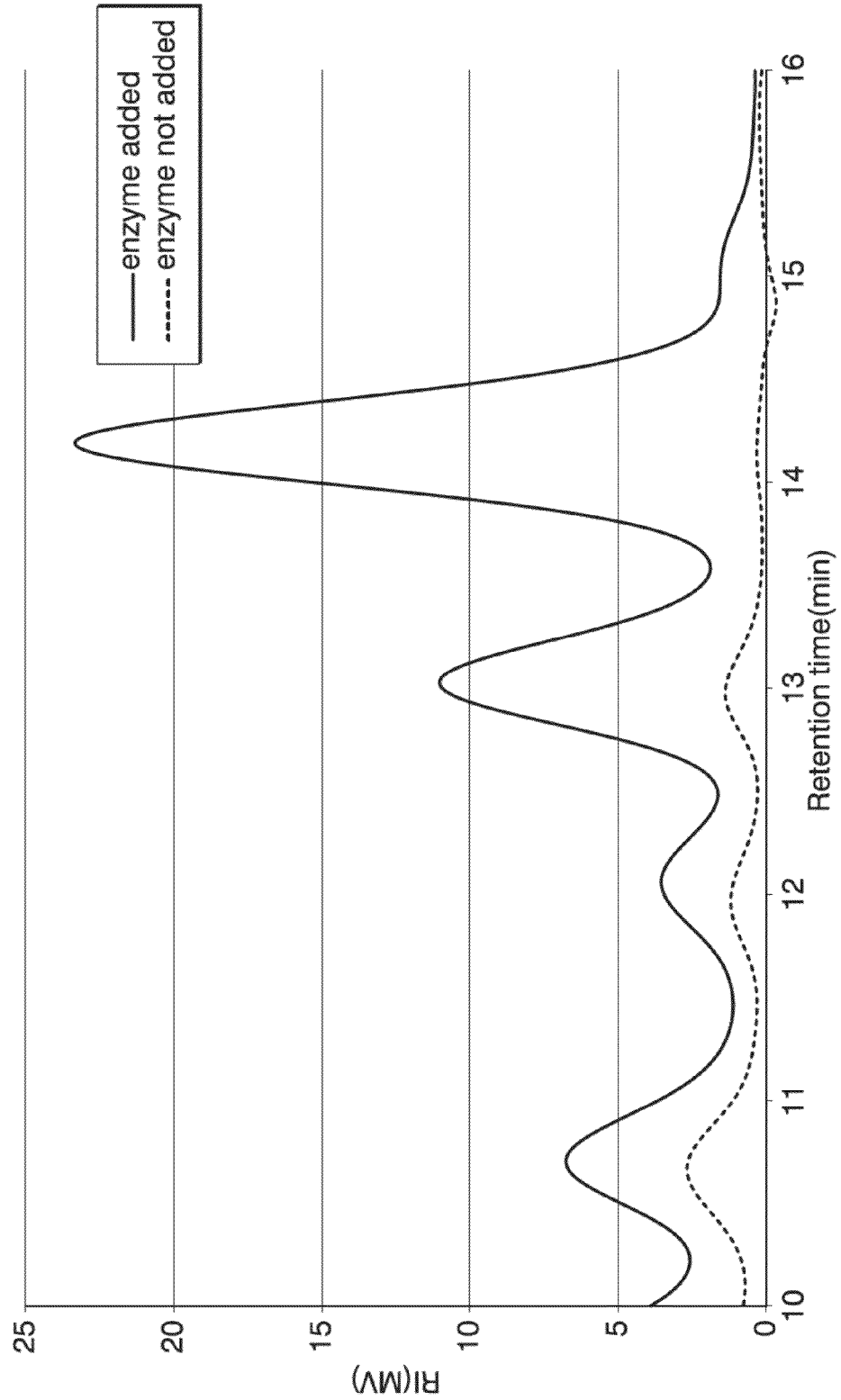
FIG. 2 is a chart indicating fractions obtained at retention times of 10 minutes to 16 minutes on an HPLC chromatogram of hydrolysates obtained by hydrolysis treatment of corn stover with an enzyme preparation in Example 1.

FIG. 2 indicates fractions obtained at retention times of 10 minutes to 16 minutes, at which disaccharides and monosaccharides are thought to elute, on an HPLC chromatogram of hydrolysates obtained from each reaction as detected with an RI detector by HPLC. In the chart, "enzyme added" indicates the results of a hydrolysate obtained following addition of the aforementioned enzyme preparation, while "enzyme not added" indicates the results of a hydrolysate treated in the same manner without adding the aforementioned enzyme preparation.

As a result, in contrast to the sugar concentration of hydrolysate (total concentration of glucose and xylose) in the case of using the commercially available hydrolysis enzyme mixture being about 1.82% by mass, the value in the case of using the enzyme preparation containing BGL was about 2.51% by mass, demonstrating that greater than 1.3 times more sugar was produced. On the basis of these results, the combined use of BGL of the present invention and other hydrolysis enzymes clearly allowed the obtaining of an enzyme mixture having a higher level of hydrolysis activity than conventional *Acremonium*-derived hydrolysis enzyme mixtures.

(6) Measurement of Enzyme Activity

<Measurement of Cellobiose Decomposition Activity>

Cellobiose decomposition activity and xylobiose activity were investigated using the enzyme sample prepared in the aforementioned section (3).

More specifically, 200 μL of a 0.03 M aqueous cellobiose solution and 190 μL of 200 mM acetic acid buffer (pH 5.5) were respectively added to two 1.5 mL volume plastic tubes and mixed well followed by pre-incubating for 5 minutes at a temperature of 30° C. Following pre-incubation, 10 μL of enzyme sample were added to one of the two tubes to initiate the enzyme reaction. After 90 minutes had elapsed since the start of the reaction, the solution in the tube was heat-treated for 5 minutes at a temperature of 95° C. to stop the enzyme reaction (duration of enzyme reaction: 90 minutes). 10 μL of enzyme sample were added to the remaining tube followed immediately by heat-treating the solution in the tube for 5 minutes at a temperature of 95° C. to stop the enzyme reaction (duration of enzyme reaction: 0 minutes).

In addition, 200 μL of a 0.014 M aqueous xylobiose solution and 190 μL of 200 mM acetic acid buffer (pH 5.5) were added to two 1.5 mL volume plastic tubes and mixed well followed by pre-incubating for 5 minutes at a temperature of 30° C., and then 100 μL of enzyme sample were added to the tube to initiate the enzyme reaction. 10 μl of enzyme sample were added to one of two tubes following pre-incubation to initiate an enzyme reaction. After 90 minutes had elapsed since the start of the reaction, the solution in the tube was heat-treated for 5 minutes at a temperature of 95° C. to stop the reaction (duration of enzyme reaction: 90 minutes). 10 μL of enzyme sample were added to the remaining tube followed immediately by heat-treating the solution in the tube for 5 minutes at a temperature of 95° C. to stop the enzyme reaction (duration of enzyme reaction: 0 minutes).

Following completion of the reactions, the four tubes were subjected to centrifugal separation treatment for 5 minutes at 15,760×g. After transferring the resulting supernatant to a fresh 1.5 mL volume plastic tube, the supernatant was filtered with a 0.2 μm (13 mm disk) filter. 0.2 mL of the filtrate were transferred to a vial, sugar was detected by carrying out HPLC measurement under the same conditions as in the aforementioned section (5), and specific activity per unit weight (U/mg) was calculated according to the equation below. Glucose and xylose (Wako Pure Chemical Industries, Ltd., respectively) were used as sugar standards for HPLC.

[Specific activity (U/mg)]=([glucose concentration (μmol/L)]×0.4/0.01)/(90×[amount of protein (mg)])

Figure 3:
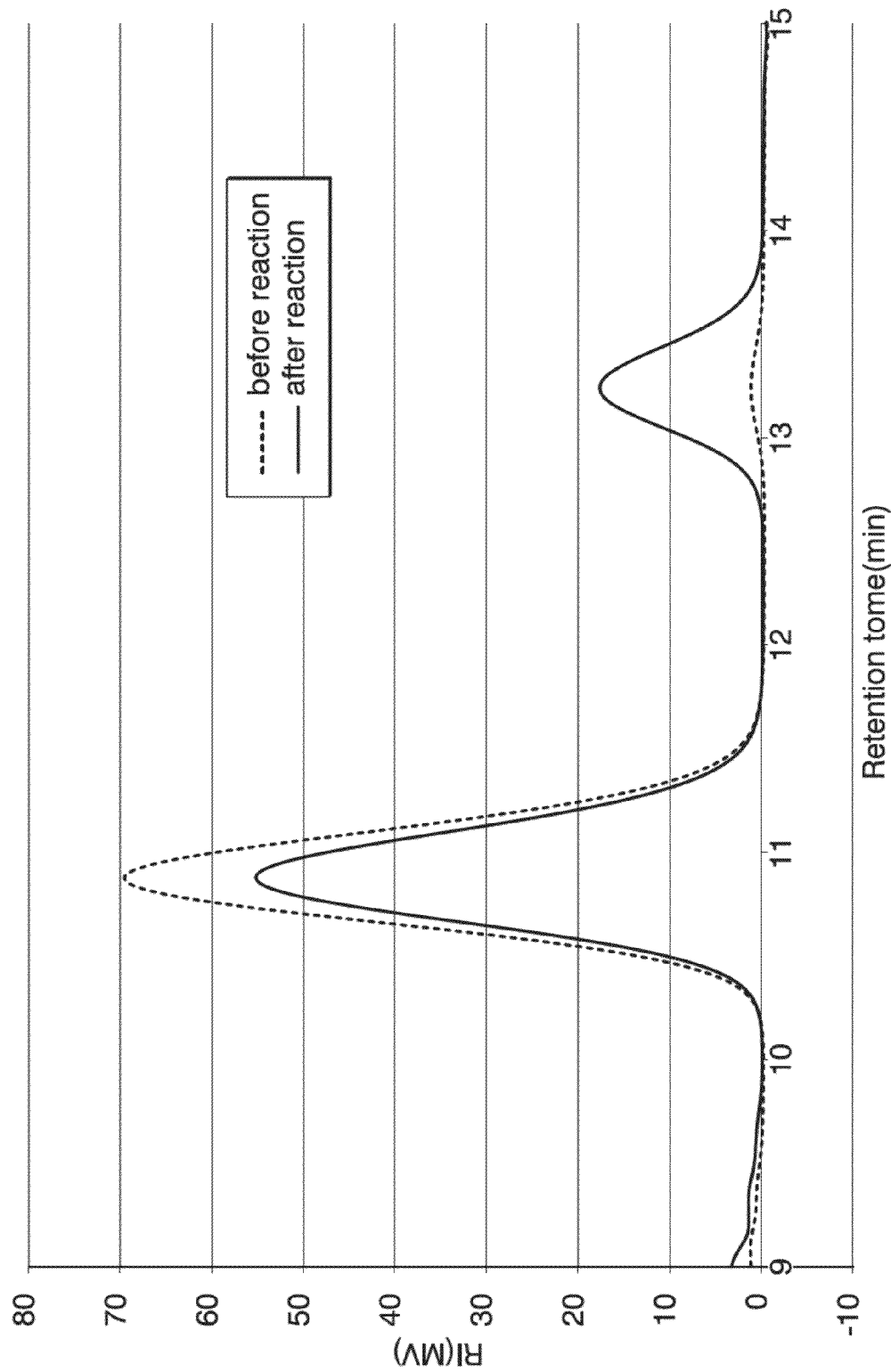
FIG. 3 is a chart indicating fractions obtained at retention times of 9 minutes to 15 minutes on an HPLC chromatogram of enzyme reaction liquids before and after an enzyme reaction of BGL using cellobiose as a substrate in Example 1.
Figure 4:
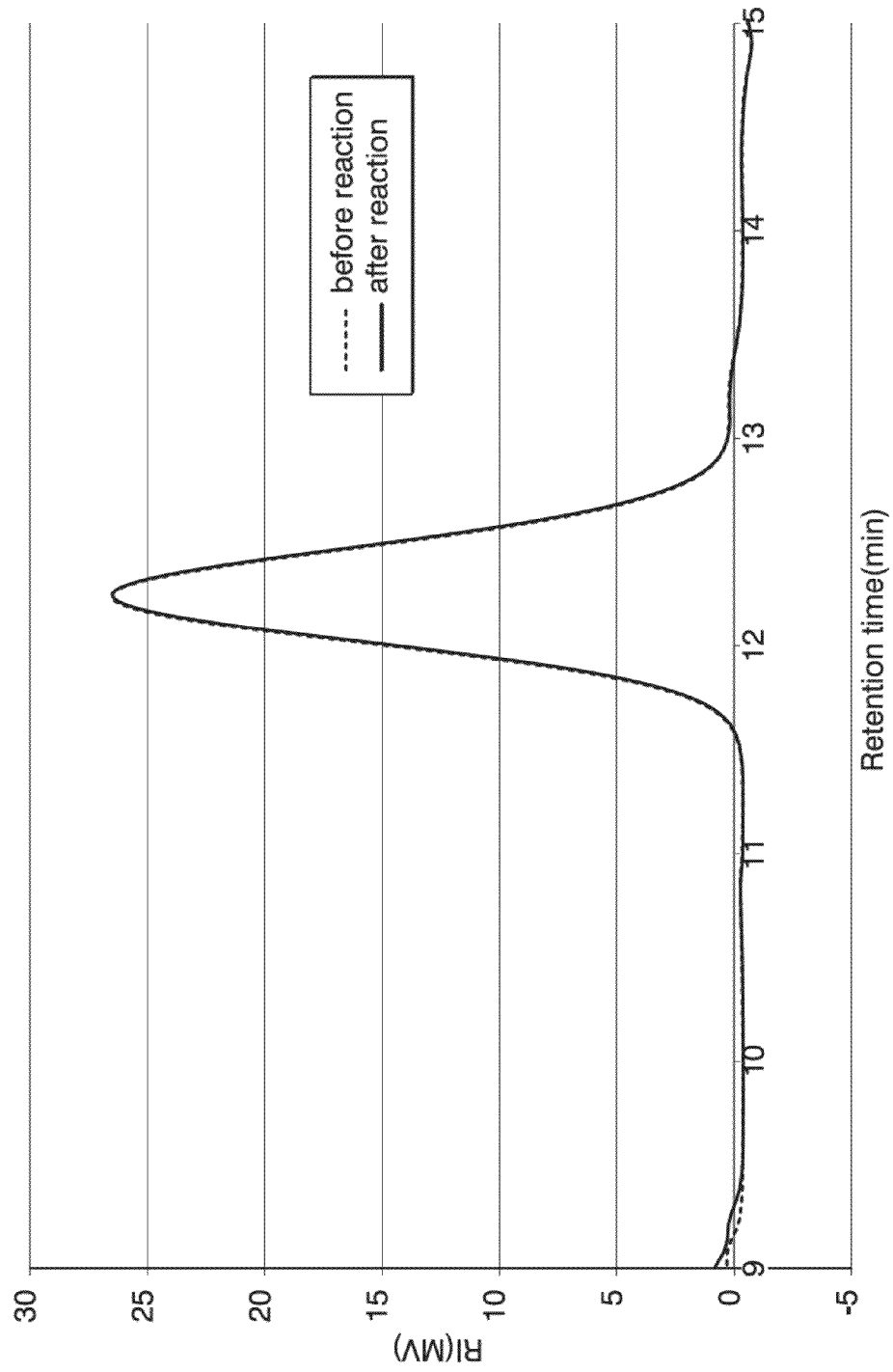
FIG. 4 is a chart indicating fractions obtained at retention times of 9 minutes to 15 minutes on an HPLC chromatogram of enzyme reaction liquids before and after an enzyme reaction of BGL using xylobiose as a substrate in Example 1.

FIGS. 3 and 4 indicate fractions obtained at retention times of 9 minutes to 15 minutes, at which disaccharides and monosaccharides are thought to elute, on HPLC chromatograms of hydrolysates obtained from each reaction as detected with an RI detector by HPLC. FIG. 3 indicates the HPLC chart for enzyme reaction liquids using cellobiose as a substrate, while FIG. 4 indicates the HPLC chart for enzyme reaction liquids using xylobiose as a substrate.

As shown in FIG. 3, in the case of using cellobiose as a substrate, if a comparison is made between the hydrolysate when the duration of the enzyme reaction is 0 minutes ("before reaction" in the chart) and the hydrolysate when the duration of the enzyme reaction is 90 minutes ("after reaction" in the chart), the peak for cellobiose observed in the vicinity of a retention time of 11 minutes is smaller for the hydrolysate after the reaction than the hydrolysate before the reaction, while the peak for glucose observed in the vicinity of a retention time of 13.3 minutes is larger, thereby confirming that cellobiose is decomposed to glucose by BGL. The specific activity of cellobiose decomposition activity of BGL was 39.86 U/mg.

On the other hand, as shown in FIG. 4, in the case of using xylobiose as a substrate, since the peak for xylobiose was only observed in the vicinity of a retention time of 12.3 minutes even for the hydrolysate when the duration of the enzyme reaction was 90 minutes ("after reaction" in the chart) in the same manner as the hydrolysate when the duration of the enzyme reaction was 0 minutes ("before reaction" in the chart), xylobiose was confirmed to not be decomposed by BGL.

(7) Temperature Dependency of PNPG Decomposition Activity

The temperature dependency of the PNPG decomposition activity of BGL was investigated using the enzyme sample prepared in the aforementioned section (3).

More specifically, after carrying out enzyme reactions in the same manner as described in <Measurement of PNPG Decomposition Activity> in the aforementioned section (4) with the exception of making the reaction temperature 30° C., 45° C., or 60° C., 200 μL aliquots of the reaction solutions were sampled from each tube followed by measuring absorbance at 420 nm (A420) and calculating the concentration of PNP in the reaction solution after the enzyme reaction from a predetermined calibration curve.

The results of measuring the PNP concentration of each reaction liquid and the values of relative activity (%) based on a value of 100% for the PNPG decomposition activity of the reaction liquid having the highest PNP concentration are shown in Table 2. The PNP concentration in the reaction liquid following the reaction is dependent upon the PNPG decomposition activity of BGL. As shown in Table 2, although BGL demonstrated a high level of PNPG decomposition activity over a temperature range of 30° C. to 45° C. and demonstrated the highest level of PNPG decomposition activity in the case of having reacted at 45° C., hardly any PNPG decomposition activity was confirmed at 60° C.

TABLE 2

| | Reaction Temperature (° C.) | | |
|---|---|---|---|
| | 30 | 45 | 60 |
| PNP Concentration (μM) | 42.29 | 58.29 | 1.14 |
| Relative Activity (%) | 72.5 | 100.0 | 2.0 |

(8) pH Dependency of PNPG Decomposition Activity

The pH dependency of the PNPG decomposition activity of BGL was investigated using the enzyme sample prepared in the aforementioned section (3).

More specifically, after carrying out enzyme reactions in the same manner as described in <Measurement of PNPG Decomposition Activity> in the aforementioned section (4) with the exception of using citrate-phosphate buffer (pH 3.0), 200 mM acetic acid buffer (pH 5.5) or 200 mM sodium phosphate buffer (pH 8.0) for the buffer mixed with the PNPG solution, 200 μL aliquots of the reaction solutions were sampled from each tube followed by measuring absorbance at 420 nm (A420) and calculating the concentration of PNP in the reaction solution after the enzyme reaction from a predetermined calibration curve.

The results of measuring the PNP concentration of each reaction liquid and the values of relative activity (%) based on a value of 100% for the PNPG decomposition activity of the reaction liquid having the highest PNP concentration are shown in Table 3. As shown in Table 3, although BGL demonstrated PNPG decomposition activity at least within the range of pH 3 to pH 5.5 and demonstrated the highest level of PNPG decomposition activity at pH 5.5, and demonstrated hardly any PNPG decomposition activity at pH 8.0.

TABLE 3

|  | Reaction Liquid pH | | |
| --- | --- | --- | --- |
|  | 3.0 | 5.5 | 8.0 |
| PNP Concentration (μM) | 18.29 | 42.29 | 1.71 |
| Relative Activity (%) | 43.2 | 100 | 4.1 |

Industrial Applicability

The β-glucosidase according to the present invention, a polynucleotide used for the production thereof, an expression vector incorporated with that polynucleotide, and a transformant introduced with that expression vector can be used, for example, in the field of energy production from cellulose-based biomass.

[Accession Number]
FERM BP-11508
[Sequence Listings]

The invention claimed is:

1. An isolated polypeptide comprising a protein having β-glucosidase activity and an amino acid sequence that is heterologous to the protein having β-glucosidase activity, wherein the amino acid sequence of the protein having β-glucosidase activity comprises an amino acid sequence selected from the group consisting of:
   (A) the amino acid sequence set forth in SEQ ID NO: 1,
   (B) the amino acid sequence of SEQ ID NO: 1, except 1-20 amino acids are deleted, substituted, or added and
   (C) an amino acid sequence having 90% or greater sequence identity with the amino acid sequence set forth in SEQ ID NO: 1, and
   wherein the heterologous amino acid sequence is at the N-terminal or C-terminal end of the protein having β-glucosidase activity and is selected from the group consisting of a signal peptide, a tag, a functional domain, and a linker sequence.

2. The polypeptide according to claim 1, which has β-glucosidase activity at pH 3.0 to pH 5.5 and a temperature of 30° C. to 45° C. and uses p-Nitrophenyl β-D-glucopyranoside as a substrate.

3. A cellulase mixture, comprising the polypeptide according to claim 1, and at least one additional cellulase.

4. A cellulase mixture, comprising the polypeptide according to claim 2, and at least one additional cellulase.

* * * * *

```
                        SEQUENCE LISTING

<160> NUMBER OF SEQ ID NOS: 13

<210> SEQ ID NO 1
<211> LENGTH: 865
<212> TYPE: PRT
<213> ORGANISM: Acremonium cellulolyticus

<400> SEQUENCE: 1

Met Arg Ala Phe Trp Trp Thr Thr Leu Leu Ser Ser Ser Val Leu Val
1               5                   10                  15

Ala Gly Leu Asp Asn Glu Ala Tyr Ser Pro Pro Tyr Tyr Pro Ser Pro
            20                  25                  30

Trp Gly Asp Gly Lys Gly Glu Trp Ala Glu Ala Tyr Glu Lys Ala Arg
        35                  40                  45

Glu Phe Val Ser Gln Leu Thr Leu Ala Glu Lys Val Asn Leu Thr Thr
    50                  55                  60

Gly Thr Gly Trp Met Gln Gly Ser Cys Val Gly Glu Thr Gly Ser Val
65                  70                  75                  80

Pro Arg Leu Gly Phe Arg Gly Leu Cys Leu Gln Asp Gly Pro Met Gly
                85                  90                  95

Ile Arg Phe Ser Asp Tyr Asn Ser Ala Phe Pro Ala Gly Val Asn Ile
            100                 105                 110

Ala Ala Thr Phe Asp Arg Ser Leu Ala Tyr Leu Arg Gly Leu Ala Met
        115                 120                 125

Gly Lys Glu Phe Asn Ser Lys Gly Val Asp Ile Gln Leu Gly Pro Val
    130                 135                 140

Ser Gly Pro Leu Gly Arg Thr Pro Glu Gly Gly Arg Asn Trp Glu Gly
145                 150                 155                 160

Phe Ser Pro Asp Pro Met Asn Thr Gly Val Met Met Ala Glu Thr Ile
                165                 170                 175

Lys Gly Ile Gln Asp Ala Gly Val Ile Ala Cys Ala Lys His Tyr Ile
            180                 185                 190

Leu Asn Glu Gln Glu His Phe Arg Leu Val Gly Glu Ala Lys Gly Tyr
        195                 200                 205

Gly Tyr Asn Ile Thr Ala Ser Ala Ser Ser Asn Val Asp Asp Arg Thr
    210                 215                 220

Met His Glu Leu Tyr Leu Trp Pro Phe Ala Asp Ala Val Arg Ala Gly
225                 230                 235                 240

Val Gly Ser Ile Met Cys Ser Tyr Asn Gln Val Asn Asn Ser Tyr Ala
                245                 250                 255

Cys Ala Asn Ser Tyr Thr Leu Asn Asn Leu Leu Lys Arg Glu Leu Asp
            260                 265                 270

Phe Gln Gly Phe Val Met Ser Asp Trp Gly Ala His Thr Ser Gly Val
        275                 280                 285
```

```
Ser Ser Thr Leu Ala Gly Leu Asp Met Ser Met Pro Gly Asp Thr Leu
    290                 295                 300
Phe Asp Ser Gly Glu Ser Tyr Trp Gly Thr Asn Leu Thr Ile Ser Val
305                 310                 315                 320
Val Asn Gly Thr Val Pro Thr Tyr Arg Ile Asp Asp Met Ala Val Arg
                325                 330                 335
Ile Met Ala Ala Tyr Tyr Lys Val Gly Arg Asp Thr Phe Gln Val Pro
                340                 345                 350
Ile Asn Phe Asn Ser Trp Thr Arg Asp Glu Tyr Gly Pro Ile Tyr Ala
            355                 360                 365
Ala Ala Gly Pro Glu Tyr Gly Ile Gly Lys Val Asn Glu Arg Val Asp
370                 375                 380
Val Arg Gly Asn His Thr Ser Leu Ile Arg Lys Ile Gly Ala Ala Ser
385                 390                 395                 400
Thr Val Leu Leu Lys Asn Thr Asn Gly Ala Leu Pro Leu Ser Gly Lys
                405                 410                 415
Glu Arg Phe Thr Ala Ile Phe Gly Ser Asp Ala Arg Ala Asp Pro Ala
                420                 425                 430
Gly Ile Asn Gly Cys Ala Asp His Gly Cys Asp Asn Gly Thr Leu Ala
            435                 440                 445
Thr Gly Trp Gly Ser Gly Thr Ser Asn Phe Pro Tyr Ile Val Thr Pro
450                 455                 460
Ala Asp Ala Ile Lys Gln Glu Ile Met Ser Lys Gly Ser Gly Ile Val
465                 470                 475                 480
Asp Ser Met Thr Asp Asp Trp Ala Tyr Asn Lys Ile Gln Ala Leu Ala
                485                 490                 495
Ser Gln Ala Asp Val Ser Leu Val Phe Val Asn Ser Asp Ser Gly Glu
                500                 505                 510
Asn Phe Ile Val Val Asp Gly Asn Glu Gly Asp Arg Asn Asn Leu Thr
            515                 520                 525
Leu Trp Arg Asp Gly Asp Ala Leu Ile Glu Thr Val Ala Ser Thr Asn
530                 535                 540
Asn Asn Thr Ile Val Val Ile His Ser Gly Gly Pro Val Leu Val Gly
545                 550                 555                 560
Asp Trp Tyr Asp Asn Pro Asn Val Thr Gly Ile Leu Trp Ala Gly Met
                565                 570                 575
Pro Gly Gln Glu Ser Gly Asn Ser Ile Thr Asp Val Leu Tyr Gly Tyr
                580                 585                 590
Val Asn Pro Gly Gly Lys Ser Pro Phe Thr Trp Gly Lys Ala Arg Glu
            595                 600                 605
Asp Tyr Ser Ala Asp Val Leu Tyr Thr Pro Asn Asn Gly Val Glu Ala
610                 615                 620
Pro Gln Ile Asp Phe Thr Glu Gly Leu Phe Val Asp Tyr Arg Gly Phe
625                 630                 635                 640
Asp Arg Ala Asn Val Thr Pro Ile Tyr Glu Phe Gly Phe Gly Leu Ser
                645                 650                 655
Tyr Thr Thr Phe Ala Tyr Ser Asn Ile Arg Val Arg Pro Leu Arg Asn
                660                 665                 670
Ala Ala Pro Tyr Thr Pro Thr Gly Leu Thr Asp Pro Ala Pro Ala
            675                 680                 685
Ala Gly Asn Phe Ser Arg Asp Trp Ser Asp Tyr Leu Phe Pro Glu Ser
690                 695                 700
Ile Arg Arg Ile Pro Leu Leu Leu Tyr Pro Trp Leu Asn Thr Thr Asp
```

```
                705                 710                 715                 720
            Pro Ala Glu Ser Ser Gly Asp Pro Asp Tyr Gly Leu Glu Ile Asp Glu
                            725                 730                 735
            Tyr Leu Pro Glu Asn Ala Thr Ser Ala Ser Pro Gln Ser Leu Leu Ala
                        740                 745                 750
            Ala Gly Gly Ala Pro Gly Gly Asn Pro Gly Leu Tyr Glu Glu Val Ala
                    755                 760                 765
            Leu Val Thr Ala Asp Ile Thr Asn Thr Gly Ser Val Val Gly Asp Glu
                770                 775                 780
            Val Pro Gln Leu Tyr Ile Ser His Gly Ser Pro Asp Asp Pro Pro Val
            785                 790                 795                 800
            Val Leu Arg Gly Phe Asp Arg Ile Ser Leu Arg Pro Lys Glu Thr Lys
                            805                 810                 815
            Glu Phe Ser Val Val Leu Thr Arg Arg Asp Ile Ser Asn Trp Asp Val
                        820                 825                 830
            Val Lys Gln Asp Trp Val Val Thr Glu Phe Pro Lys Thr Val Tyr Val
                    835                 840                 845
            Gly Ser Ser Arg Glu Leu Arg Leu Glu Ala Arg Leu Pro Asp Leu
                850                 855                 860
            Ser
            865

<210> SEQ ID NO 2
<211> LENGTH: 2598
<212> TYPE: DNA
<213> ORGANISM: Acremonium cellulolyticus

<400> SEQUENCE: 2
atgcgtgcat tctggtggac gacgttattg agttcctcgg tactggttgc aggactggat         60
aatgaagcat attcaccacc atattatccc tcgccttggg gcgacggcaa aggcgagtgg        120
gcagaagctt atgagaaggc gagagaattc gtgagccaac ttactcttgc tgagaaggtg        180
aatttgacga cgggtactgg gtggatgcaa ggctcctgcg tcggcgaaac aggctcagtc        240
ccaagacttg gattccgagg tctctgcctt caagatgggc ctatgggcat ccgcttcagc        300
gactacaact ccgccttccc cgccggtgtc aacatagccg caacctttga ccgctccctc        360
gcgtacctcc gtggcctcgc aatgggcaaa gaattcaact ccaagggcgt cgacatccaa        420
ctcggccccg tctccggccc tttgggcaga cacccgaagg aggccgaaac tgggaaggg         480 ttcagtcccg acccgatgaa tacggtgtgt atgatggctg agacaataaa aggatacaa         540 gatgcgggtg tgattgcgtg cgcgaaacat tatattctga atgagcagga acattttagg        600 ttggtgggg  aggcgaaggg gtatgggtat aatattactg cgagcgcgag tagtaacgtt        660 gatgataggac gatgcatga gttgtattta tggccatttg cagacgcagt acgcgcaggt        720
gttggatcaa tcatgtgctc ctacaaccaa gtcaacaaca gctacgcatg cgcaaacagc        780
tacacgctaa acaacctcct caaacgcgaa ctcgactttc agggcttcgt catgagtgac        840
tggggcgcac acacatccgg cgtaagcagt acgcttgccg gactcgacat gtccatgccc        900
ggcgacactc tcttcgactc tggcgaatcg tactggggta ctaatttgac catttcagtc        960
gtcaacggca ctgtcccgac gtataggatt gatgatatgg cggttcgtat catggctgca       1020
tattacaaag tcggccggga cacattccag gttcctatca acttcaattc gtggactcgt       1080
gatgagtatg tccgatttta tgcagcggca ggaccggagt atgggattgg taaagtcaat       1140
gagcgtgtcg atgtacgcgg taatcatacc tcgttgattc gcaagattgg tgccgcgagt       1200
```

```
acggtcctcc tgaagaacac aaacggcgcc cttccgctca gcggcaaaga gagattcaca    1260
gccatatttg gctcggatgc tcgtgccgat ccagcaggta tcaatggctg cgctgatcat    1320
ggctgcgaca acggcacact cgccacaggt tggggagcg gtacatctaa ttttccctac     1380
atcgtgactc cagcagacgc catcaagcaa gaaatcatga gcaaaggctc cggcatcgtc    1440
gattccatga ccgatgactg ggcatacaac aaaatccaag ccctcgcttc ccaagcagac    1500
gtatcacttg tgtttgtgaa ctctgactca ggcgaaaact tcatcgtcgt tgacggcaac    1560
gaaggagatc gcaacaatct caccctctgg cgagacgggg atgcactcat cgaaaccgtc    1620
gcttccacaa ataacaacac catcgtcgta atccacagcg gcggtcccgt tcttgtgggt    1680
gattggtacg acaatccaaa tgtaaccgga atcctctggg caggtatgcc aggccaagag    1740
agcggaaact ccatcacaga cgttttgtac ggttatgtca accccggtgg caagagtccc    1800
tttacatggg gaaaagcgcg tgaggattac tccgcagatg tcctgtatac acctaacaac    1860 gggggttgaag caccacaaat tgatttcacg gagggtctgt tcgttgatta tcgtggcttt    1920
gatagagcaa atgtcacgcc aatttatgaa tttgggtttg gtttgagtta tacgacattc    1980
gcatactcca atatcagggt tcgaccactt cgaaacgcag ctccctacac acccacgacc    2040
gggctcacgg atcctgcacc ggcagctggc aatttcagca gagattggtc ggattatctc    2100
ttccccgaat ccattcgcag aatcccttg cttctgtatc catggctaaa acgacagat     2160 ccagccgaat cgtctggcga ccctgactac ggcctcgaga tagacgaata tctacccgag    2220
aacgcgacct ccgcctctcc ccaatccta ctcgcagctg gaggcgcacc aggcggaaat     2280
ccaggcttgt acgaggaagt cgctcttgtg actgctgata ttaccaacac cggcagtgtc    2340 gtggggatg aggttcctca actttatata tcccacggct cccccgacga tcccccgtt     2400 gtccttcgag gtttcgatcg catcagtcta cgacccaagg agacgaaaga gttcagcgtc    2460
gtcctgacgc gccgcgacat ctcgaactgg gatgttgtta gcaggactg ggttgtgacg     2520 gagtttccca agacggttta tgtgggcagt tcgtcgcgcg aattacggtt ggaggcgagg    2580
ttgcctgatt tatcttaa                                                  2598
```

```
<210> SEQ ID NO 3
<211> LENGTH: 2885
<212> TYPE: DNA
<213> ORGANISM: Acremonium cellulolyticus
<220> FEATURE:
<221> NAME/KEY: CDS
<222> LOCATION: join(1..56,115..259,321..418,467..859,911..2582,
      2651..2885)
<223> OTHER INFORMATION: /gene="BGL", /product="BGL"
<220> FEATURE:
<221> NAME/KEY: exon
<222> LOCATION: <1..56
<223> OTHER INFORMATION: /number=1, /gene="BGL"
<220> FEATURE:
<221> NAME/KEY: intron
<222> LOCATION: 57..114
<223> OTHER INFORMATION: /number=1, /gene="BGL"
<220> FEATURE:
<221> NAME/KEY: exon
<222> LOCATION: 115..259
<223> OTHER INFORMATION: /number=2, /gene="BGL"
<220> FEATURE:
<221> NAME/KEY: intron
<222> LOCATION: 260..320
<223> OTHER INFORMATION: /number=2, /gene="BGL"
<220> FEATURE:
<221> NAME/KEY: exon
<222> LOCATION: 321..418
<223> OTHER INFORMATION: /number=3, /gene="BGL"
```

```
<220> FEATURE:
<221> NAME/KEY: intron
<222> LOCATION: 419..466
<223> OTHER INFORMATION: /number=3, /gene="BGL"
<220> FEATURE:
<221> NAME/KEY: exon
<222> LOCATION: 467..859
<223> OTHER INFORMATION: /number=4, /gene="BGL"
<220> FEATURE:
<221> NAME/KEY: intron
<222> LOCATION: 860..910
<223> OTHER INFORMATION: /number=4, /gene="BGL"
<220> FEATURE:
<221> NAME/KEY: exon
<222> LOCATION: 911..2582
<223> OTHER INFORMATION: /number=5, /gene="BGL"
<220> FEATURE:
<221> NAME/KEY: intron
<222> LOCATION: 2583..2650
<223> OTHER INFORMATION: /number=5, /gene="BGL"
<220> FEATURE:
<221> NAME/KEY: exon
<222> LOCATION: 2651..2885
<223> OTHER INFORMATION: /number=6, /gene="BGL"

<400> SEQUENCE: 3
atgcgtgcat tctggtggac gacgttattg agttcctcgg tactggttgc aggactggtg      60
agctctacaa tcacccatac tttgttagac cgtacctgtc taaccgcagg aataggataa     120
tgaagcatat tcaccaccat attatccctc gccttgggc gacggcaaag gcgagtgggc      180
agaagcttat gagaaggcga gagaattcgt gagccaactt actcttgctg agaaggtgaa     240
tttgacgacg ggtactgggt gagtctatct ttgaactgag gtgcaattgt ggtaaattaa     300
attgacccgg atgaaaaagg tggatgcaag gctcctgcgt cggcgaaaca ggctcagtcc     360
caagacttgg attccgaggt ctctgccttc aagatgggcc tatgggcatc cgcttcagta     420
cgtatctcat cgcaacaaac aaaacacaca actaaacaat gacaaggcga ctacaactcc     480
gccttccccg ccgtgtcaa catagccgca acctttgacc gctccctcgc gtacctccgt     540
ggcctcgcaa tgggcaaaga attcaactcc aagggcgtcg acatccaact cggccccgtc     600
tccggcccct tgggcagaac acccgaagga ggccgaaact gggaagggtt cagtcccgac     660
ccgatgaata cgggtgtgat gatggctgag acaataaaag ggatacaaga tgcgggtgtg     720
attgcgtgcg cgaaacatta tattctgaat gagcaggaac attttaggtt ggtgggggag     780
gcgaagggt atgggtataa tattactgcg agcgcgagta gtaacgttga tgataggacg     840
atgcatgagt tgtatttatg gtttgttcat tccctattcg tctggtgatt tcaatctgct     900
aatgttcaaa ggccatttgc agacgcagta cgcgcaggtc ttggatcaat catgtgctcc     960
tacaaccaag tcaacaacag ctacgcatgc gcaaacagct acacgctaaa caacctcctc    1020
aaacgcgaac tcgactttca gggcttcgtc atgagtgact ggggcgcaca cacatccggc    1080
gtaagcagta cgcttgccgg actcgacatg tccatgcccg gcgacactct cttcgactct    1140
ggcgaatcgt actgggggtac taatttgacc atttcagtcg tcaacggcac tgtcccgacg    1200
tataggattg atgatatggc ggttcgtatc atggctgcat attacaaagt cggccgggac    1260
acattccagg ttcctatcaa cttcaattcg tggactcgtg atgagtatgg tccgatttat    1320
gcagcggcag gaccggagta tgggattggt aaagtcaatg agcgtgtcga tgtacgcggt    1380
aatcatacct cgttgattcg caagattggt gccgcgagta cggtcctcct gaagaacaca    1440
aacggcgccc ttccgctcag cggcaaagag agattcacag ccatatttgg ctcggatgct    1500
cgtgccgatc cagcaggtat caatggctgc gctgatcatg gctgcgacaa cggcacactc    1560
```

```
gccacaggtt gggggagcgg tacatctaat tttccctaca tcgtgactcc agcagacgcc    1620
atcaagcaag aaatcatgag caaaggctcc ggcatcgtcg attccatgac cgatgactgg    1680
gcatacaaca aaatccaagc cctcgcttcc aagcagacg tatcacttgt gtttgtgaac    1740
tctgactcag gcgaaaactt catcgtcgtt gacggcaacg aaggagatcg caacaatctc    1800
accctctggc gagacgggga tgcactcatc gaaaccgtcg cttccacaaa taacaacacc    1860
atcgtcgtaa tccacagcgg cggtcccgtt cttgtgggtg attggtacga caatccaaat    1920
gtaaccggaa tcctctgggc aggtatgcca ggccaagaga gcggaaactc catcacagac    1980
gttttgtacg gttatgtcaa ccccggtggc aagagtccct ttacatgggg aaaagcgcgt    2040
gaggattact ccgcagatgt cctgtataca cctaacaacg gggttgaagc accacaaatt    2100
gatttcacgg agggtctgtt cgttgattat cgtggctttg atagagcaaa tgtcacgcca    2160
atttatgaat ttgggtttgg tttgagttat acgacattcg catactccaa tatcagggtt    2220
cgaccacttc gaaacgcagc tccctacaca cccacgaccg ggctcacgga tcctgcaccg    2280
gcagctggca atttcagcag agattggtcg gattatctct tccccgaatc cattcgcaga    2340
atccctttgc ttctgtatcc atggctaaac acgacagatc cagccgaatc gtctggcgac    2400
cctgactacg gcctcgagat agacgaatat ctacccgaga acgcgacctc cgcctctccc    2460
caatccttac tcgcagctgg aggcgcacca ggcggaaatc caggcttgta cgaggaagtc    2520
gctcttgtga ctgctgatat taccaacacc ggcagtgtcg tggggatga ggttcctcaa    2580 cttgtacctt tcccccattt accaccccca cttttctcttc gatgttctat gctgacccgg    2640
tatgatggta gtatatatcc cacgctccc ccgacgatcc ccccgttgtc cttcgaggtt    2700
tcgatcgcat cagtctacga cccaaggaga cgaaagagtt cagcgtcgtc ctgacgcgcc    2760
gcgacatctc gaactgggat gttgttaagc aggactgggt tgtgacggag tttcccaaga    2820
cggtttatgt gggcagttcg tcgcgcgaat tacggttgga ggcgaggttg cctgatttat    2880
cttaa                                                                2885
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 4
tcctccaagt tacccatgcg tgcattctgg                                        30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 5
cgcttcgtcg accccttaag ataaatcagg                                        30

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Primer.

<400> SEQUENCE: 6
atgctcggga gctttggatt tcctacgtct tc        32

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Primer.

<400> SEQUENCE: 7
atgcatatgt cgagagtgtt gtgtgggtca acg        33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Primer.

<400> SEQUENCE: 8
atggtcgacg aagcgtaaca ggatagccta gac        33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Primer.

<400> SEQUENCE: 9
atgcccgaga gtaacccatt cccggttctc tag        33

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer.

<400> SEQUENCE: 10
atggctagca gatctcgcgg cagggttgac        30

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Primer.

<400> SEQUENCE: 11
atggtcgacc ccgggtaact tggaggacgg aagaaaagag        40

<210> SEQ ID NO 12
<211> LENGTH: 529
<212> TYPE: PRT
<213> ORGANISM: Acremonium cellulolyticus
<220> FEATURE:
<223> OTHER INFORMATION: Cellobiohydrolase1

<400> SEQUENCE: 12

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

-continued

```
Ala Glu Thr His Pro Ser Leu Ser Trp Ser Thr Cys Lys Ser Gly Gly
         35                  40                  45

Ser Cys Thr Thr Asn Ser Gly Ala Ile Thr Leu Asp Ala Asn Trp Arg
 50                  55                  60

Trp Val His Gly Val Asn Thr Ser Thr Asn Cys Tyr Thr Gly Asn Thr
 65                  70                  75                  80

Trp Asn Ser Ala Ile Cys Asp Thr Asp Ala Ser Cys Ala Gln Asp Cys
                 85                  90                  95

Ala Leu Asp Gly Ala Asp Tyr Ser Gly Thr Tyr Gly Ile Thr Thr Ser
             100                 105                 110

Gly Asn Ser Leu Arg Leu Asn Phe Val Thr Gly Ser Asn Val Gly Ser
         115                 120                 125

Arg Thr Tyr Leu Met Ala Asp Asn Thr His Tyr Gln Ile Phe Asp Leu
130                 135                 140

Leu Asn Gln Glu Phe Thr Phe Thr Val Asp Val Ser His Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Ser Asn Asn Ala Asn Thr Gly
    210                 215                 220

Ile Gly Asn His Gly Ala Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Ser Val Cys Thr Thr Asp Ala Cys Gly Gly Thr Tyr Ser Ser Asp
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300

Thr Lys Pro Phe Thr Val Val Thr Gln Phe Val Thr Asn Asp Gly Thr
305                 310                 315                 320

Ser Thr Gly Ser Leu Ser Glu Ile Arg Arg Tyr Tyr Val Gln Asn Gly
                325                 330                 335

Val Val Ile Pro Gln Pro Ser Ser Lys Ile Ser Gly Ile Ser Gly Asn
            340                 345                 350

Val Ile Asn Ser Asp Tyr Cys Ala Ala Glu Ile Ser Thr Phe Gly Gly
        355                 360                 365

Thr Ala Ser Phe Ser Lys His Gly Gly Leu Thr Asn Met Ala Ala Gly
    370                 375                 380

Met Glu Ala Gly Met Val Leu Val Met Ser Leu Trp Asp Asp Tyr Ala
385                 390                 395                 400

Val Asn Met Leu Trp Leu Asp Ser Thr Tyr Pro Thr Asn Ala Thr Gly
                405                 410                 415

Thr Pro Gly Ala Ala Arg Gly Thr Cys Ala Thr Thr Ser Gly Asp Pro
            420                 425                 430

Lys Thr Val Glu Ala Gln Ser Gly Ser Ser Tyr Val Thr Phe Ser Asp
        435                 440                 445

Ile Arg Val Gly Pro Phe Asn Ser Thr Phe Ser Gly Gly Ser Ser Thr
```

```
                450             455             460
Gly Gly Ser Thr Thr Thr Ala Ser Arg Thr Thr Thr Ser Ala
465                 470             475             480

Ser Ser Thr Ser Thr Ser Ser Thr Ser Thr Gly Thr Gly Val Ala Gly
                485             490             495

His Trp Gly Gln Cys Gly Gly Gln Gly Trp Thr Gly Pro Thr Thr Cys
                500             505             510

Val Ser Gly Thr Thr Cys Thr Val Val Asn Pro Tyr Tyr Ser Gln Cys
                515             520             525

Leu

<210> SEQ ID NO 13
<211> LENGTH: 226
<212> TYPE: PRT
<213> ORGANISM: Acremonium cellulolyticus
<220> FEATURE:
<223> OTHER INFORMATION: Endoglucanase

<400> SEQUENCE: 13

Met Lys Leu Thr Phe Leu Leu Asn Leu Ala Val Ala Ala Ser Ala Gln
1               5                   10                  15

Gln Ser Leu Cys Ser Gln Tyr Ser Ser Tyr Thr Ser Gly Gln Tyr Ser
                20                  25                  30

Val Asn Asn Asn Leu Trp Gly Glu Ser Ser Gly Ser Gly Ser Gln Cys
                35                  40                  45

Thr Tyr Val Asn Ser Ile Ser Ser Gly Val Ser Trp Ser Thr Thr
    50                  55                  60

Trp Asn Trp Ser Gly Gly Ser Thr Ser Val Lys Ser Tyr Ala Asn Ser
65                  70                  75                  80

Gln Leu Ser Gly Leu Thr Lys Lys Leu Val Ser Asn Leu Gln Ser Ile
                85                  90                  95

Pro Thr Ser Val Gln Trp Ser Tyr Ser Asn Thr Asn Ile Val Ala Asp
                100                 105                 110

Val Ser Tyr Asp Leu Phe Thr Ala Ala Asp Ile Asn His Val Thr Tyr
                115                 120                 125

Ser Gly Asp Tyr Glu Leu Met Ile Trp Leu Gly Lys Tyr Gly Gly Ala
                130                 135                 140

Gln Pro Leu Gly Ser Gln Ile Gly Thr Ala Asn Val Gly Gly Ala Thr
145                 150                 155                 160

Trp Gln Leu Trp Tyr Gly Val Asn Gly Ser Gln Lys Thr Tyr Ser Phe
                165                 170                 175

Val Ala Ser Ser Gln Thr Thr Ser Trp Asn Gly Asp Ile Leu Gln Phe
                180                 185                 190

Phe Lys Tyr Leu Gln Ser Asn Gln Gly Phe Pro Ala Ser Ser Gln Tyr
                195                 200                 205

Leu Ile Asp Leu Gln Phe Gly Thr Glu Pro Phe Thr Gly Ser Gln Thr
                210                 215                 220

Thr Leu
225
```